United States Patent
Lee et al.

(10) Patent No.: US 11,851,475 B2
(45) Date of Patent: Dec. 26, 2023

(54) MEMBRANE-TYPE METALLOPROTEASE INHIBITORY PROTEIN AND PHARMACEUTICAL AND PHARMACEUTICAL COMPOSITION CONTAINING SAME, AND RESPECTIVE USES THEREOF

(71) Applicant: XI'AN JIAOTONG-LIVERPOOL UNIVERSITY, Jiangsu (CN)

(72) Inventors: Meng Huee Lee, Jiangsu (CN); Bingjie Jiang, Jiangsu (CN); Jian Liu, Jiangsu (CN)

(73) Assignee: XI'AN JIAOTONG-LIVERPOOL UNIVERSITY, Jiangsu (CN)

( * ) Notice: Subject to any disclaimer, the term of this patent is extended or adjusted under 35 U.S.C. 154(b) by 745 days.

(21) Appl. No.: 16/960,010

(22) PCT Filed: Dec. 20, 2018

(86) PCT No.: PCT/CN2018/122305
§ 371 (c)(1),
(2) Date: Jul. 2, 2020

(87) PCT Pub. No.: WO2019/134526
PCT Pub. Date: Jul. 11, 2019

(65) Prior Publication Data
US 2023/0159624 A1    May 25, 2023

(30) Foreign Application Priority Data

Jan. 3, 2018 (CN) .......................... 201810004200.2
Oct. 26, 2018 (CN) .......................... 201811257903.2

(51) Int. Cl.
| C07K 14/81 | (2006.01) |
|---|---|
| A61K 35/33 | (2015.01) |
| A61K 38/57 | (2006.01) |
| A61K 38/00 | (2006.01) |

(52) U.S. Cl.
CPC .......... C07K 14/8146 (2013.01); A61K 35/33 (2013.01); A61K 38/57 (2013.01)

(58) Field of Classification Search
CPC .... C07K 14/8146; C07K 14/81; A61K 35/33; A61K 38/57; A61K 38/00
See application file for complete search history.

(56) References Cited

U.S. PATENT DOCUMENTS

| 2002/0115187 A1 * | 8/2002 | Greene .............. C07K 14/8146 435/7.1 |
|---|---|---|
| 2017/0115275 A1 | 4/2017 | Rege et al. |

FOREIGN PATENT DOCUMENTS

| CN | 1153477 | 7/1997 | |
|---|---|---|---|
| CN | 1863532 | 11/2006 | |
| CN | 102300987 | 12/2011 | |
| CN | 102300987 A | 12/2011 | |
| CN | 10334314 | 10/2013 | |
| CN | 105316405 | 2/2016 | |
| CN | 108314727 | 7/2018 | |
| CN | 108314727 A | 7/2018 | |
| CN | 109260228 | 1/2019 | |
| CN | 109394786 | 3/2019 | |
| CN | 110662966 | 1/2020 | |
| WO | 03502343 | 6/2003 | |
| WO | 2004075835 | 9/2004 | |
| WO | WO-2007117444 A2 * | 10/2007 | .......... C12N 15/111 |
| WO | 2008019142 A2 | 2/2008 | |
| WO | 2017075537 A1 | 5/2017 | |

OTHER PUBLICATIONS

Bolduc et al., "Peptide Self-Assembled Monolayers for Label-Free and Unamplified Surface Plasmon Resonance Biosensing in Crude Cell Lysate," Analytical Chemistry, 2009, 81: 6779-3788. (Year: 2009).*
Metalloproteinase inhibitor 1 [Papio anubis] NCBI Reference Sequence: XP_003917687.1 Jul. 26, 2017.
Office Action in CN 201810004200.2 (dated Jan. 14, 2021).
Meng-Huee Lee, Delineating the molecular basis of the inactivity of tissue inhibitor of metalloproteinase-2 against tumor necrosis factor-alpha-converting enzyme 2004.
Bingjie Jiang, Ensnaring membrane type 1-matrix metalloproteinase (MT1-MMP) with tissue inhibitor of metalloproteinase (TIMP) 2using the haemopexin domain of the protease as a carrier a targeted approach in cancer inhibition 2017.
Bingjie Jiang, Targeting a Designer TIMP-1 to the Cell Surface for Effective MT1-MMP Inhibition: A Potential Role for the Prion Protein in Renal Carcinoma Therapy 2019.
Bingjie Jiang, Translocating a High-Affinity Designer TIMP-1 to the Cell Membrane for Total Renal Carcinoma Inhibition: Putting the Prion Protein to Good Use 2019.

* cited by examiner

*Primary Examiner* — Julie Ha (57) ABSTRACT

Disclosed is a membrane-type metalloprotease inhibitory protein T1$^{PraTACE}$ and use thereof, which can be used for preparing drugs targeting MT1-MMP or TACE endonuclease. Also disclosed are an antitumor pharmaceutical composition comprising BHK-21 cells and an artificial basal membrane which expresses T1$^{PraTACE}$ protein.

4 Claims, 7 Drawing Sheets

Specification includes a Sequence Listing.

TIMP-1:
MAPFEPLASGILLLLWLIAPSRACTCVPPHPQTAFCNSDLVIRAKFVGT
PEVNQTTLYQRYEIKMTKMYKGFQALGDAADIRFVYTPAMESVCGYF
HRSHNRSEEFLIAGKLQDGLLHITTCSFVAPWNSLSLAQRRGFTKTYT
VGCEECTVFPCLSIPCKLQSGTHCLWTDQLLQGSEKGFQSRHLACLPR
EPGLCTWQSLRSQIA*

T1ProTACE:
MAPFEPLASGILLLLWLIAPSRACTCSPPHPQTAFCNSDLVIRAKFVGT
PEVNQSPEGTQRYEIKMTKMYKGFQALGDAADIRFVYTPAMESLCGY
FHRSHNRSEEFLIAGKLQDGLLHITLCSFVAPWNSLSLAQRRGFTKTYT
VGCEECTVFPCLSIPCKLQSGTHCLWTDQLLQGSEKGFQSRHLACLPR
EPGLCTWQSLRSQIAQYERESQAYYQRGSSMVLFSPPVILLISFLIFLI
VG*

MetAlaProPheGluProLeuAlaSerGlyIleLeuLeuLeuLeuTrpLeuIleAlaProSerArgAlaCysThrCysSerPr
oProHisProGlnThrAlaPheCysAsnSerAspLeuValIleArgAlaLysPheValGlyThrProGluValAsnGlnGlyP
roPheGlyThrGlnArgTyrGluIleLysMetThrLysMetTyrLysGlyPheGlnAlaLeuGlyAspAlaAlaAspIleAr
gPheValTyrThrProAlaMetGluSerLeuCysGlyTyrPheHisArgSerHisAsnArgSerGluGluPheLeuIleAla
GlyLysLeuGlnAspGlyLeuLeuHisIleThrLeuCysSerPheValAlaProTrpAsnSerLeuSerLeuAlaGlnArgA
rgGlyPheThrLysThrTyrThrValGlyCysGluGlnCysThrValPheProCysLeuSerIleProCysLysLeuGlnSer
GlyThrHisCysLeuTrpThrAspGlnLeuLeuGlnGlySerGluLysGlyPheGlnSerArgHisLeuAlaCysLeuPro
ArgGluProGlyLeuCysThrTrpGlnSerLeuArgSerGlnIleAlaGlnTyrGluArgGluSerGlnAlaTyrTyrGlnA
rgGlySerSerMetValLeuPheSerSerProProValIleLeuLeuIleSerPheLeuIlePheLeuIleValGly

MEMBRANE-TYPE METALLOPROTEASE INHIBITORY PROTEIN AND PHARMACEUTICAL AND PHARMACEUTICAL COMPOSITION CONTAINING SAME, AND RESPECTIVE USES THEREOF

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,926 Byte ASCII (Text) file named "sequence3.TXT," created on Dec. 21, 2020.

TECHNICAL FIELD

The present application relates to the field of biological medicine, and specifically, relates to a membrane-type metalloprotease inhibitory protein, and a pharmaceutical and pharmaceutical composition containing the same, and respective uses thereof.

BACKGROUND

At present, there are three types of cancer treatment approaches.
1. Chemotherapy: The most common side effects of chemotherapy include nausea and vomiting, alopecia, immunosuppression and loss of appetite.
2. Radiotherapy: The side effects of radiotherapy are usually milder than those of chemotherapy. Cutaneous reactions such as skin peeling, erythema, and fibrosis are side effects associated with radiotherapy. Furthermore, this treatment approach requires settings such as specialized treatment equipment, hospitals and the like.
3. Immunotherapy: The common side effects of immunotherapy are fatigue, fever, weakness, nausea, body aches, hypertension and other symptoms associated with immunization.

Therefore, the existing cancer treatment approaches have many defects and drawbacks. Membrane Type 1-Matrix Metalloproteinase (MT1-MMP) and TNF-α Converting Enzyme (TACE) are zinc ion-dependent transmembrane endopeptidases. Both proteases are involved in the degradation and remodeling of Extracellular Matrix (ECM) and play an important role in the progression of tumor invasion and metastasis by releasing various active factors needed to induce cell growth. In term of catalytic activity, MT1-MMP can degrade a variety of extracellular matrix and basal membrane macromolecules such as Type I, II, and III collagen, laminin, fibronectin, fibrin and some important adhesion molecules. The enzyme can also activate signaling molecules required for the invasion and spreading of cancer cells such as polysaccharides, CD44, RANKL, MUC1 that play crucial roles in promoting tumor invasion and metastasis.

TACE is a member of the "A Disintegrin and Metalloproteinase (ADAM)" family, also known as ADAM-17. The versatility of TACE is shown by its ability to shed and release a large variety of transmembrane ligands such as growth factors (TNF-α, TGF-α, and HG-EGF), receptors (TNFR II, EGFR, IL-6R, and Notch-1), adhesion molecules (ICAM-1, V-CAM-1, and L-selectin) and even the prion protein associated with the neurodegenerative disease transmissible spongiform encephalopathy (TSE). By modulating the release of these molecules, TACE can affect the occurrence, progression and metastasis of tumors. Under normal physiological conditions, the activities of the MMP and ADAM proteases are regulated by the endogenous inhibitors termed tissue inhibitors of metalloproteases (TIMPs). There are four known types of human TIMPs namely. TIMP-1, 2, 3 and 4. TIMPs are small proteins with molecular weights between 21 kDa to 25 kDa. Structure-wise, TIMPs are composed of two distinctive domains, that is, an N-terminal inhibitory domain composed of five anti-parallel β-sheets (with molecular weight of about 15 kDa) and a C-terminal domain with no fixed structure (molecular weight approximately 8 kDa) (Protein Data Bank crystal #1BR9, #1UEA). TIMPs can bind to the catalytic cleft of the target proteases via their wedge-shaped N-terminal domains to form 1:1 stoichiometric conjugates (examples include PDB crystal #4ILW, #3V96 and #3CKI) and by so doing, inhibiting the MMPs. Despite sharing a common tertiary configuration, each TIMP has its own unique profile of MMP inhibition. For instance, MT1-MMP is sensitive to TIMP-2, -3 and -4 but insensitive to TIMP-1. Interestingly, TIMP-3 is the only member of the TIMP family that demonstrates an inhibitory activity against TACE. With the exception of TIMP-3, the TIMPs are all highly soluble secretory proteins.

As the first member of the TIMP family to be isolated in the 1980s, TIMP-1 is a secreted glycoprotein with a molecular weight of approximately 25 kDa. Despite its lack of inhibitory potency against MT1-MMP and TACE, TIMP-1 has been shown to exhibit cell potentiation activity in cancer cells.

Wild type TIMP-1 protein (i.e. primary TIMP-1) has several disadvantages that include: (1) wild type TIMP-1 is a soluble secreted protein; there is no evidence that showed that TIMP-1 can interact with MT1-MMP and TACE, be it intracellularly or extracellularly; (2) TIMP-1 has no intrinsic ability to bind and inhibit MT1-MMP and TACE; the $K_i^{app}$ values of TIMP-1 for MT1-MMP and TACE are known to be well over 150 nM; and (3) the undesirable cell potentiation effect of TIMP-1 in promoting malignant cell growth has greatly curtailed its potential as a cancer therapeutic.

SUMMARY

The following is a summary of the subject matter described. This summary is not intended to limit the scope of the claims.

The problem to be solved by the present application is to provide a modified membrane-type metalloprotease inhibitory protein named $T1^{PraTACE}$ based on the metalloprotease inhibitory protein TIMP in the existing art.

The first aspect of the present application provides a modified membrane-type metalloprotease inhibitory protein named $T1^{PraTACE}$ that has an amino acid sequence as shown in Seq ID No. 1.

The second aspect of the present application provides uses of the membrane-type metalloprotease inhibitory protein $T1^{PraTACE}$ in the preparation of an antitumor drug with MT1-MMP and TACE endoproteinases as the intended targets.

The third aspect of the present application provides a drug, which includes the membrane-type metalloprotease inhibitory protein $T1^{PraTACE}$ and a pharmaceutically acceptable excipient.

In a preferred technical solution of the present application, the excipient is a carrier, a solvent, an emulsifier, a dispersant, a humectant, an adhesive, a stabilizer, a colorant or a flavor.

In a preferred technical solution of the present application, the drug is an injection, a tablet, a capsule, an electuary, a drop, a granule or an ointment.

In the above technical solutions, the preparation of a pharmaceutical composition targeting MT1-MMP or TACE endoproteinase may be performed by adding general pharmaceutical auxiliary components into the protein $T1^{Pr\alpha TACE}$ with a purity of more than 98% (mass percentage) for the preparation of tablets, capsules, electuary, drops, freeze-dried products, granules, ointments or injections.

Pharmaceutical Formulation and Administration

According to conventional methods known in the art for preparing various dosage forms, $T1^{Pr\alpha TACE}$ protein can be formulated into solutions, emulsions, suspensions, dispersions, or inclusion complexes such as cyclodextrins in suitable pharmaceutical solvents or carriers, or into pills, tablets, lozenges, suppositories, sachets, dragees, granules, powders, reconstituted powders or capsules along with solid carriers. The pharmaceutical composition of the embodiment may be administered by a suitable route of delivery, for example, by oral, parenteral, rectal, nasal, local, or ocular delivery or by inhalation. Preferably, the composition is formulated for intravenous or oral administration.

For oral administration, the drug may be provided in solid form, such as tablets or capsules, or formulated as solutions, emulsions or suspensions. Oral tablets may include an active component mixed with pharmaceutically acceptable compatible excipients such as diluents, disintegrants, binding agents, lubricants, sweeteners, flavoring agents, colorants and preservatives. Suitable inert fillers include sodium carbonate and calcium carbonate, sodium phosphate and calcium phosphate, lactose, starch, sugar, glucose, methyl cellulose, magnesium stearate, mannitol, sorbitol and the like. Exemplary liquid oral excipients include ethanol, glycerol, water and the like. Exemplary disintegrants include starch, polyvinylpyrrolidone (PVP), sodium starch glycolate, microcrystalline cellulose and alginic acid. Binding agents may include starch and gelatin. The lubricant, if exists, may be magnesium stearate, stearic acid or talc. If needed, the tablets may be coated with a material such as glyceryl monostearate or glyceryl distearate to delay absorption in the gastrointestinal tract, or may be enteric coated. Oral formulations may exist in the following forms: in the form of discrete units, such as capsules, cachets, or tablets, each containing a predetermined amount of the active component; in the form of powders or granules; in the form of solutions or suspensions in an aqueous liquid or a non-aqueous liquid; or in the form of oil-in-water liquid emulsions or water-in-oil liquid emulsions. The active component may also be formulated as a bolus, electuary or paste.

Oral capsules include hard and soft gelatin capsules. To prepare hard gelatin capsules, the active component may be mixed with a solid, semi-solid or liquid diluent. The preparation of soft gelatin capsules may be accomplished by mixing the active component with the following materials: water, oils such as peanut oil or olive oil, liquid paraffin wax, a mixture of monoglycerides and diglycerides of short chain fatty acids, polyethylene glycol 400, or propylene glycol.

Tablets may be made by compression or molding, and optionally one or more accessory components may be added to the tablet. Tablets may be prepared by compressing in a suitable machine the active component in a free-flowing form such as powders or granules, and optionally mixed with an adhesive (e.g., povidone, gelatin, hydroxypropylmethyl cellulose), lubricant, inert diluent, preservative, disintegrant (e.g., sodium starch glycolate, crospovidone, croscarmellose sodium), surfactant or dispersant. Molded tablets may be made by molding in a suitable machine a mixture of powdered compounds moistened with an inert liquid diluent. The tablets may optionally be coated or scored, and may be formulated so that the active components therein are released slowly or controllably, which, for example, may be achieved by using hydroxypropylmethyl cellulose in varying proportions to acquire the desired release profile.

Oral liquids may be in the following form: suspensions, solutions, emulsions, or syrups, or may be lyophilized or presented as a dry product which can be reconstituted with water or other suitable vehicles before being administered. Such liquid compositions may optionally include the following materials, pharmaceutically acceptable excipients such as suspending agents (e.g., sorbitol, methyl cellulose, sodium alginate, gelatin, hydroxyethyl cellulose, carboxymethyl cellulose, aluminum stearate gel, etc.); non-aqueous vehicles such as oils (e.g., almond oil or fractionated coconut oil), propylene glycol, ethanol or water; preservatives (e.g., methyl or propyl parahydroxybenzoic acid or sorbic acid); wetting agents such as lecithin; and, if needed, flavouring agents or colourants.

For parenteral administration, including intravenous, intramuscular, intraperitoneal, intranasal or subcutaneous routes, the composition may be formulated in the following forms: sterile aqueous solutions or suspensions buffered to appropriate pH and isotonicity, or parenterally acceptable oils. Suitable aqueous vehicles include Ringer's solution and isotonic sodium chloride. Such forms may be presented as follows: in a unit-dose form, such as ampoules or disposable injection devices; in a multi-dose form, such as a vial from which appropriate doses can be drawn; or in a solid form or pre-concentrate capable of being used for preparing injectable formulations. Formulations suitable for parenteral administration including intravenous administration include the following forms: aqueous and non-aqueous sterile injection solutions which may contain antioxidants, buffers, bacteriostats, and solutes which render the formulation isotonic with the blood of the intended recipient; and aqueous and non-aqueous sterile suspensions which may contain suspending agents and thickening agents. The formulations may be stored in unit-dose or multi-dose containers, for example sealed ampoules and vials, and may be stored in a freeze-dried (lyophilized) condition requiring only the addition of the sterile liquid carrier such as water for injections immediately prior to use. Extemporaneous injection solutions and suspensions may be prepared from sterile powders, granules and tablets described above.

Preferred unit dosage formulations are referred to those containing a daily dose or unit, a daily sub-dose or an appropriate fraction of an active component.

Dosage and Administration Route

The doses of $T1^{Pr\alpha TACE}$ administered to an individual (e.g., a human) described herein may vary depending on the particular composition, method of administration, and stage of the disease. The amount thereof should be sufficient to produce desirable responses. In some embodiments, the amount of the composition is a therapeutically effective amount. In some embodiments, the amount of the composition is a prophylactically effective amount. In some embodiments, the total amount of $T1^{Pr\alpha TACE}$ in the composition is below the level that induces toxicological effects (i.e., this level is above a clinically acceptable toxicity level), or at a level where the potential side effects of the composition may be controlled or tolerated when administered to the individual.

In some embodiments, the amount of the $T1^{Pr\alpha TACE}$ protein in the drug ranges from about 0.5 mg to about 5 mg, from about 5 mg to about 10 mg, from about 10 mg to about 15 mg, from about 15 mg to about 20 mg, from about 20 mg to about 25 mg, from about 20 mg to about 50 mg, from about 25 mg to about 50 mg, from about 50 mg to about 75 mg, from about 50 mg to about 100 mg, from about 75 mg to about 100 mg, from about 100 mg to about 125 mg. In some embodiments, the amount of the $T1^{PraTACE}$ protein administered in a drug is at least about 0.1 mg/kg, 0.5 mg/kg, 1 mg/kg, 2.5 mg/kg, 5 mg/kg, 7.5 mg/kg, 10 mg/kg, 15 mg/kg, or 20 mg/kg per day.

The effective dosage of the $T1^{PraTACE}$ protein can be changed according to the route of administration, the age and weight of the patient, the severity of the disease and other related factors. The recommended dosage for oral administration is 10-2000 mg/time, 1-2 times each day. The recommended dosage for parenteral administration is 5-500 mg/time, once each day.

Despite retaining the basic three-dimensional structure of a TIMP-1 protein, the "MMP-binding ridge" (the actual site binding to the target MMPs) and carboxy-terminus of $T1^{PraTACE}$ had been subjected to extensive site-directed mutation to the extent that the resultant $T1^{PraTACE}$ has clear, demonstrable inhibitory activities for both MT1-MMP and TACE. In addition, experimental data reveal that $T1^{PraTACE}$ is very effective in preventing human renal carcinoma cell CaKi-1 from developing in mouse xenograft model in vivo. The advantages of $T1^{PraTACE}$ in the present application are as follows.

(1) Wild type TIMP-1 has no significant inhibitory effect on MT1-MMP and TACE. In contrast, $T1^{PraTACE}$ is a very potent inhibitor against both the proteases. Kinetic analysis showed that the $K_i^{app}$ values of $T1^{PraTACE}$ are as low as 7.70 nM for MT1-MMP and 0.14 nM for TACE. Unlike the water-soluble TIMP-1, the newly developed $T1^{PraTACE}$ is anchored to the cell membrane. Immunofluorescent staining indicate that $T1^{PraTACE}$ interacts readily with both MT1-MMP or TACE on the cell surface.

(2) Tumorigenesis experiments in mouse xenograft model indicate that, unlike wild type TIMP-1. $T1^{PraTACE}$ lacks cell potentiation activity.

(3) Experiments in mouse model further confirm the anti-proliferative and anti-metastatic effects of $T1^{PraTACE}$ against human renal cancer cells Caki-1.

A fourth aspect of the present application provides an anti-tumor pharmaceutical composition, which includes BHK-21 cells expressing the $T1^{PraTACE}$ protein and an artificial basal membrane.

In a preferred technical solution of the present application, the final concentration of BHK-21 cells expressing the $T1^{PraTACE}$ protein (named BHK+$T1^{PraTACE}$ cells) is 300,000 cells/mL to 625,000 cells/mL.

In a preferred technical solution of the present application, the mass percentage of the artificial basal membrane is between 30 wt % to 60 wt %.

In a preferred technical solution of the present application, the anti-tumor pharmaceutical composition includes Dulbecco's medium (DMEM) with 2% to 10% of fetal bovine serum.

In a preferred technical solution of the present application, the anti-tumor pharmaceutical composition includes: BHK-21 cells expressing the $T1^{PraTACE}$ protein with a final concentration of between 300,000 cells/mL to 625.000 cells/mL; 30 wt % to 60 wt % of artificial basal membrane: and Dulbecco's medium (DMEM) with 5% of fetal bovine serum.

In a preferred technical solution of the present application, the final concentration of BHK-21 cells expressing $T1^{PraTACE}$ protein is between 500,000 cells/mL and 625,000 cells/mL.

In a preferred technical solution of the present application, the mass percentage of the artificial basal membrane is between 50 wt % to 60 wt % and more preferably, the artificial basal membrane is Matrigel® matrigel.

The fifth aspect of the present aspect of the present application provides the use of a the above-mentioned pharmaceutical composition in the preparation of a drug for the treatment or prevention of tumors. The tumor is selected from renal cancer, cervical cancer, breast cancer, lung cancer, rectal cancer, ovarian cancer, liver cancer, gastric cancer and leukemia. Preferably, the renal cancer comprises renal cell carcinoma.

In a preferred technical solution of the present application, the pharmaceutical composition functions at a temperature between 24° C. to 37° C.

The preparation method or use method of the pharmaceutical composition of the present application is as follows: a certain amount of BHK+$T1^{PraTACE}$ cells is mixed with a certain volume of 30% to 60% liquefied artificial basal membrane to generate a cell-basal membrane mixture, before a certain amount of cancer cells is added to render the concentration of the two cell types between 300,000 cells/mL to 625,000 cells/mL. The mixture is inoculated in a culture plate within the temperature range of 24° C. and 37° C. to allow the cell-basal membrane mixture to solidify. Dulbecco's Modified Eagle Medium (DMEM) containing 2% to 10% of fetal bovine serum is added to the plate after the mixture has solidified. The above-mentioned cancer cells are preferably labeled with red fluorescent protein (RFP).

Artificial basal membrane extract is commonly used in 3D cell culture to simulate in vivo microenvironment. Matrigel® (BD Bioscience) is a reconstituted basal membrane extract originated from Engelbreth-Holm-Swarm (EHS) mouse sarcoma known to be rich in extracellular matrix proteins. Since Matrigel contains a large quantity of extracellular matrix proteins such as laminin (60%), collagen (30%), internal actin (8%), heparin sulphate glycoprotein and growth factors (FGF, EGF, TGF-β) required for cell stimulation and signaling, the extract can simulate the structure, composition, physical properties and functions of an in vivo basal membrane environment, thereby providing an environment favorable for cell growth even under in vitro setting (Hughes, Postovit et al. 2010, Benton, Kleinman et al. 2011, Benton, Arnaoutova et al. 2014).

BHK-21 is a fibroblastic cell strain derived from the kidney of neonatal hamster established by Stoker and Macpherson in 1961 (Stoker and Macpherson, 1961). BHK-21 cells are sensitive to viral infection and the cell line has been widely used as a host for viral propagation and biopharmaceutical production for many years.

Disclosed in this patent application is a composition named "Matrigel®:Baby Hamster Kidney (BHK)-21" that could be employed to encapsulate and inhibit cancer cell proliferation in vitro. As the name suggests, the compound is composed of basal membrane extracts (Matrigel®) and BHK-21 cells (the final concentration of Matrigel® is 30% wt to 60% wt and the concentration of BHK-21 is between 300,000 cells/mL to 625,000 cells/mL). Research data (unpublished) show that Matrigel®:BHK-21 composition constituted under such specification are capable of encapsulating and inhibiting cancer cell proliferation in vitro.

Also disclosed in this patent application is a strategy to further improve the efficacy of Matrigel®:BHK-21 composition through the incorporation of T1$^{PraTACE}$. By replacing unmodified BHK-21 cells with a genetically modified BHK-21 cell variant that stably expresses the T1$^{PraTACE}$ protein (named "BHK+T1$^{PraTACE}$"), the anti-cancer effect of the Matrigel®:BHK-21 composition can be further enhanced. Evidence shows that the modified Matrigel®:BHK+T1$^{PraTACE}$ composition is more effective in wrapping and killing cancer cells than the previously established model.

BRIEF DESCRIPTION OF DRAWINGS

FIG. 2 is a schematic view of the inhibitory mechanism of T1$^{PraTACE}$ on MT1-MMP and TACE. As shown, T1$^{PraTACE}$ is made up of two functionally distinct domains, namely:
  (1) An N-terminal "inhibitory domain" that binds directly to the catalytic clefts of MT1-MMP ($K_i^{app}$ 7.70 nM, Table 1) and TACE ($K_i^{app}$ 0.14 nM, Table 1).
  (2) A C-terminal glycosylphosphatidylinositol (GPI) anchor that tethers the TIMP to the cell membrane and thus, to the vicinity of MT1-MMP and TACE.

FIG. 3 summarizes the findings from two independent immunostaining experiments carried out under non-permeabilized condition; wherein FIG. 3A demonstrates the co-localization of T1$^{PraTACE}$ and MT1-MMP on the cell membrane.

DETAILED DESCRIPTION

Specific embodiments of the present application is described in detail below with reference to the drawings.

I. MATERIALS

1. Experimental Animal
NOD-SCID mice (Beijing Vital River Laboratory Animal Technology Co., Ltd.)
2. Drugs and Reagents
2.1 Drugs: puromycin; basal membrane Matrigel®, from BD Bioscience; BHK-21 cell strain (Shanghai cell bank GNHa10). CaKi-1 cells (Shanghai cell bank TChu135). HeLa cells (Shanghai cell bank TChu187); medium: 5% fetal bovine serum, penicillin-streptomycin solution (1×) and DMEM medium.
2.2 Reagents: TIMP-1 antibody (Abcam), MT1-MMP antibody (Abcam), TACE antibody (Abcam), Alexa Fluor488 anti-mouse secondary antibody (Invitrogen), Alexa Fluor555 anti-rabbit secondary antibody (Invitrogen), ProLong® Antifade reagent with DAPI (Thermo Fisher), 38% paraformaldehyde (Sigma), porcine Oregon Green® 488-conjugated gelatin (Thermoscientific), lipofectamine transfection kit (Invitrogen), propylene glycol methyl ether acetate (PMA), phosphate substrate (Sigma), TNF-α Elisa kit (Sino Bio), EcoR I endonuclease (Thermoscientific), Xho I endonuclease (Thermoscientific), Apa I endonuclease (Thermoscientific), Nde I endonuclease (Thermoscientific), related gene sequences and primers synthesized by Sangon Biotech (Shanghai) Co. Ltd.
2.3 Instruments: LS-55 fluorescence spectrometer (PerkinElmer Life Sciences). C1-Si laser confocal microscope (Nikon), upright fluorescence microscope (Nikon), inverted fluorescence microscope (Nikon), multifunctional Microplate Reader (Thermoscientific); FACSArialI cell sorter (BD Bioscience), automatic cell counter (Invitrogen).

II. EXAMPLE

Example 1: Inhibitory Effects of T1$^{PraTACE}$ on MT1-MMP and TACE

The study was performed according to the methods disclosed in the following references:
1. Lee M H, Rapti M. Knauper V. Murphy G. Threonine 98, the pivotal residue of tissue inhibitor of metalloproteinases (TIMP)-1 in metalloproteinase recognition. *J. Biol. Chem.* 2004:279(17):17562-69.
2. Lee M H, Rapti M. Murphy G. Unveiling the surface epitopes that render tissue inhibitor of metalloproteinase-1 inactive against membrane type 1-matrix metalloproteinase. *J. Biol. Chem.* 2003; 278(41):40224-30.
Specific procedures are as follows.
1. MT1-MMP (R&D, 918-MP-010) and TACE (R&D, 930-ADB-010) proteins were purchased from R&D Systems.

2. The N-terminal (i.e. the inhibitory) domain of wild type TIMP-1 (GenBank: S68252.1) was prepared by PCR amplification using the following primers (synthesized by Sangon Biotech): forward primer: 5'-GAAC-CATATGTGCACCTGTGTACCACCCCACCCA-3' (Nde I restriction site is marked, as shown in Seq ID No. 3), and reverse primer: 5'-TCAACTGCTCGAGT-TAATGATGATGATGATGATGATGGGC-TATCTGGGACCGC AGGGACTG-3' (Xho I restriction site is underlined, as shown in Seq ID No. 4).
3. Likewise, the N-terminal domain of $T1^{PraTACE}$ was prepared by PCR amplification, wherein the forward primer was 5'-GAAC CATATGTGCACCTGTTCCC-CACCCCACCCA-3' as shown in Seq ID No. 5, and the reverse primer is the same to that for wild type TIMP-1.
4. TIMP-1 and $T1^{PraTACE}$ PCR amplicons were digested with Nde I and Xho I and cloned into a pRSET-c expression vector (Invitrogen) to generate expression plasmids bearing the TIMP cDNAs. The plasmids were sequenced (Sangon Biotech (Shanghai) Co. Ltd.) to ensure that no unwanted mutation had been accidentally introduced during the PCR amplification process.
5. pRSET-c plasmids containing the N-terminal domains of TIMP-1 and $T1^{PraTACE}$ were transformed into BL21 (DE3)pLys competent cells for protein expression.
6. The binding affinities of TIMP-1 and $T1^{PraTACE}$ were tested on MT1-MMP and TACE with a LS-55 fluorescence spectrofluorimeter.

Results are shown in Table 1.

TABLE 1

Inhibitory Affinities of Wild Type TIMP-1 (inhibitory domain) and $T1^{PraTACE}$ (inhibitory domain) on MT1-MMP and TACE ($K_i^{app}$, unit: nM)

|  | TIMP-1 | $T1^{PraTACE}$ |
|---|---|---|
| MT1-MMP | 178 ± 20 | 7.70 ± 2.84 |
| TACE | 356 ± 87 | 0.14 ± 0.06 |

Kinetic analysis shows that the binding affinities of $T1^{PraTACE}$ on MT1-MMP and TACE was substantially stronger than that of the wild type TIMP-1.

Table 1 shows the inhibitory effects of wild type TIMP-1 and $T1^{PraTACE}$ on MT1-MMP and TACE. By measuring the changes in the intensity of the fluorescent substrate (Mca-K-P-L-G-L-Dpa-A-R-NH2, R&D Systems) with a LS-55 fluorescence spectrofluorimeter, the affinity of the TIMPs on MT1-MMP and TACE were measured and calculated. Data show that the affinity of $T1^{PraTACE}$ for MT1-MMP and TACE ($K_i^{app}$ was 7.70 nM and 0.14 nM, respectively) was significantly higher than that of the wild type TIMP-1 ($K_i^{app}$ >150 nM in both occasions).

Example 2: Co-Localization of $T1^{PraTACE}$ with MT1-MMP and TACE on the Cell Surface 1. Lentiviruses carrying TIMP-1 and $T1^{PraTACE}$ cDNAs were prepared as follows:
   a. Wild type TIMP-1 (GenBank: S68252.1) was amplified by PCR using the following primers: forward primer: 5'-GCAGCAGAATTCACCATGGCCCCCTTT-GAGCCCCTGGCT-3' (EcoR I restriction site is underlined, as shown in Seq ID No. 6), and reverse primer: 5'-TCAACTGGGGCCCTTAGGCTATCTGGGAC-CGCAGGGACTG-3' (Apa I restriction site is underlined, as shown in Seq ID No. 7).
   b. Likewise, $T1^{PraTACE}$ cDNA was similarly prepared, wherein the forward primer was identical to that for TIMP-1, the reverse primers were composed of three overlapping primers ①5'-GGCCTGAGATTCCCT-CTCGTACTGGGCTATCTGGGACCGCAGGGAC-TG-3', as shown in Seq ID No. 8; ② 5'-CACAGGTGGGGAGGAGAAGAGGAC-CATGCTCGATCCTCTCTGGTAATAGGCCTGA GATTCCCTCTCGTACTG-3', as shown in Seq ID No. 9; and ③ 5'-TAAACGGGCCCTCATCCCACTATT-AGGAAGATGAGGAAAGAGATCAGGAGGATCA CAGGTGGGGAGGAGAAG AGGAC-3', as shown in Seq ID No. 10. In short, one forward and three (overlapping) reverse primers were used to generate $T1^{PraTACE}$ cDNA that carries a GPI signal peptide at the C-terminus.
   c. The PCR amplicons were digested with EcoR I and Apa I for insertion into pLVX-puro (Takara) vector. The plasmids were sequenced to ensure that no unwanted mutation had been introduced during the PCR amplification process.
   d. pLVX-puro plasmids containing TIMP-1 and $T1^{PraTACE}$ cDNAs were extracted and purified with a Maxiprep plasmid kit (AXYGEN) for downstream packaging application.
   e. Lenti-X One-Shot Packaging mix (Takara 631276) was dissolved in 0.5 ml sterile water and mixed with 10 μg of TIMP-1 or $T1^{PraTACE}$ plasmid DNA.
   f. The packaging-plasmid mix were added to Lenti-X 293T cells in 10 cm cell culture plates to allow for viral packaging in a humidified cell culture incubator. Media containing lentivirus was harvested 3 days later.
   g. CaKi-1 cells were transduced with lentivirus containing TIMP-1/$T1^{PraTACE}$ and stably transduced cells were obtained by selection with puromycin (1 μg/mL).

2. Co-localization of $T1^{PraTACE}$ with MT1-MMP and TACE on the Cell Surface

The study was performed according to the method disclosed in the following document: Jiang B, Zhang Y, Liu J, et al. Ensnaring membrane type 1-matrix metalloproteinase (MT1-MMP) with tissue inhibitor of metalloproteinase (TIMP)-2 using the haemopexin domain of the protease as a carrier: a targeted approach in cancer inhibition. *Oncotarget*, 2017, 8(14): 22685.

Specific procedures are as follows.
(1) CaKi-1 cells stably expressing TIMP-1 and $T1^{PraTACE}$ were seeded on a chamber slide and cultured for 2 days at 37° C.
(2) The cells were fixed in 4% paraformaldehyde for 10 minutes followed by rinsing with PBS for 3 times.
(3) Following a 2-hour blocking with 5% bovine serum albumin (BSA)/PBS, two antibody pairs TIMP-1+MT1-MMP or TIMP-1+TACE were added to the slide for overnight incubation at 4° C.
(4) The slide was rinsed three times with PBS, 5 minutes each.
(5) Anti-mouse/rabbit secondary antibodies were added to the slide. Incubation was allowed at room temperature for 2 hours.
(6) Following rinsing with PBS, the slides were mounted in ProLong® Antifade reagent and inspected under a confocal laser scanning microscope.

Figure 1:
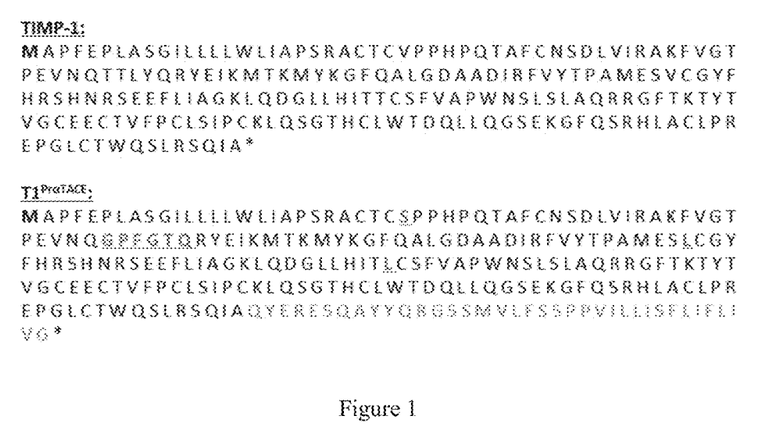
FIG. 1 is a schematic view of the amino acid sequences of T1$^{PraTACE}$ and wild type TIMP-1.
Figure 2:
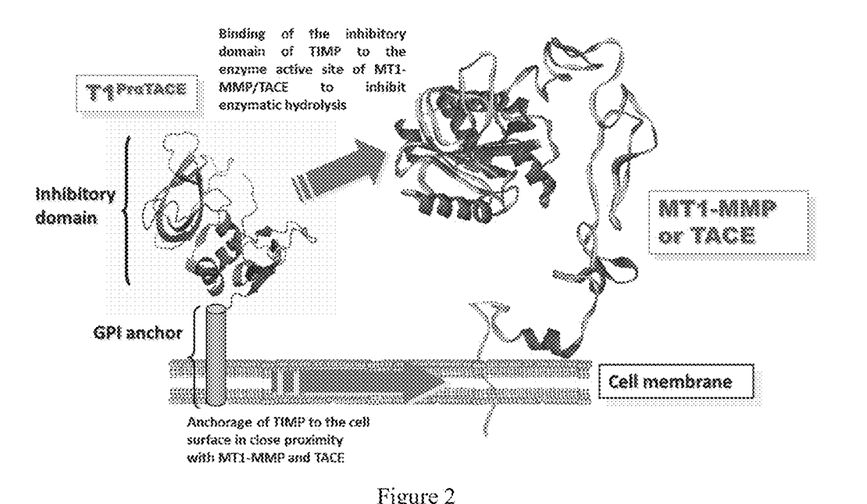
Figure 3A:
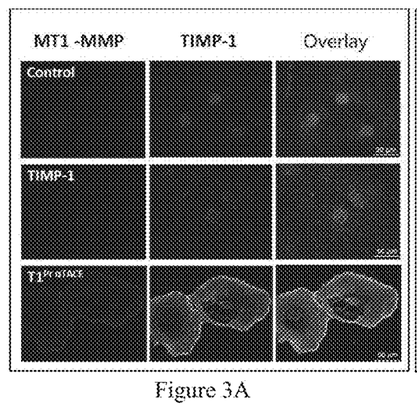
Figure 3B:
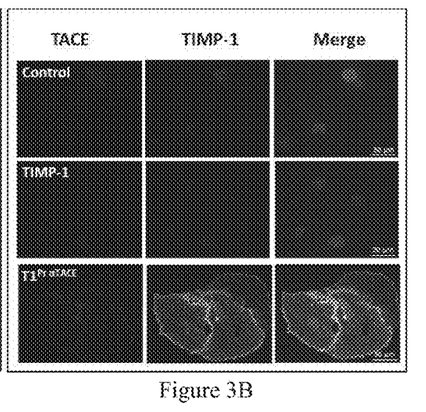
FIG. 3B shows the same interaction between T1$^{PraTACE}$ and TACE on the cell surface. Both experiments are conducted on CaKi-1 cells stably transduced with the TIMP.

Result: As shown in FIGS. 3A and 3B: owe largely to its high solubility, wild type TIMP-1 was not detected on the cell membrane. In contrast, $T1^{PraTACE}$ was found to be present in abundance on the cell surface and in association with MT1-MMP or TACE.

Example 3: T1$^{PraTACE}$ Inhibits Gelatin Degradation by MT1-MMP in HT1080 Cells The study was performed according to the methods disclosed in the following document: Jiang B, Zhang Y, Liu J, et al. Ensnaring membrane type 1-matrix metalloproteinase (MT1-MMP) with tissue inhibitor of metalloproteinase (TIMP)-2 using the haemopexin domain of the protease as a carrier: a targeted approach in cancer inhibition. *Oncotarget*, 2017, 8(14): 22685.

Specific procedures are as follows:
1. HT1080 cells were infected with lentivirus bearing TIMP-1 and T1$^{PraTACE}$ genes as described under Example 2.1. Using the same procedures, HT1080 cells stably expressing TIMP-1 and T1$^{PraTACE}$ were generated.
2. Nunc® LabTek II Chamber Slides® were pre-coated with fluorescent gelatin (0.5 mg/mL; overnight).
3. Following rinsing with PBS, the cells were fixed with 4% paraformaldehyde for 10 minutes.
4. The slides were rinsed with PBS for 5 times to ensure the complete removal of paraformaldehyde
5. HT1080 cells stably transduced with TIMP-1 or T1$^{PraTACE}$ were seeded on the chamber slides and incubated overnight at 37° C.
6. The cells were fixed with paraformaldehyde and washed with PBS following the procedure in steps (3) and (4) above.
7. Cell membrane permeabilization was carried out by incubation with cold methanol for 20 min; wash slides with PBS for three times.
8. The slides were blocked with 5% BSA in 0.3% Triton X-100 before MT1-MMP antibody was added for overnight incubation at 4° C.
9. Following washing with PBS, the cells were incubated with a secondary antibody at room temperature for 2 hours.

Figure 4:
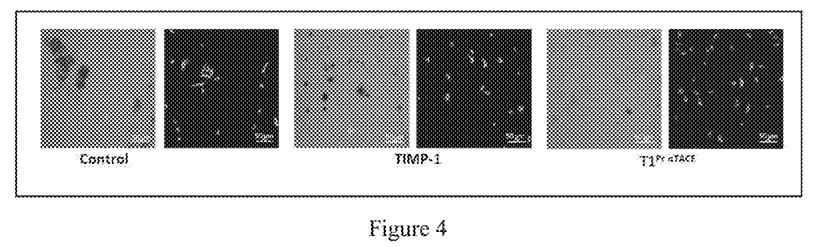
FIG. 4 highlights the ability of T1$^{PraTACE}$ in blocking gelatin film degradation by MT1-MMP on a fluorescent gelatin-coated plate in T1$^{PraTACE}$-transduced HT1080 fibrosarcoma cells.
Figure 5A:
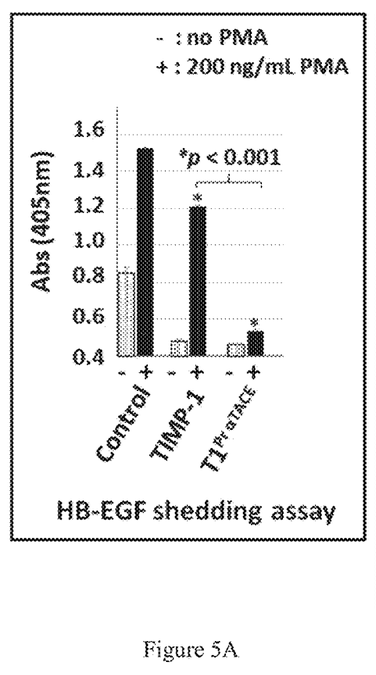
FIGS. 5A and 5B are findings from two independent cell-based assays that highlight the potency of T1$^{PraTACE}$ in preventing TACE-mediated HB-EGF and TNF-α shedding in T1$^{PraTACE}$-transduced HT1080 fibrosarcoma cells.
Figure 5B:
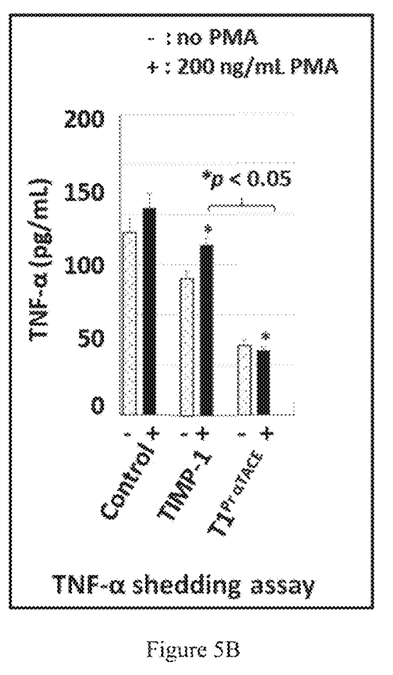

Result: FIG. 4: HT1080 cells stably expressing T1$^{PraTACE}$ demonstrates a much lower gelatinolytic ability than wild type TIMP-1-expressing cells.

Example 4: T1$^{PraTACE}$ Inhibits TACE-Mediated TNF-α and HB-EGF Shedding

The study was performed according to the method disclosed in the following document: Duan J X, Rapti M, Tsigkou A, Lee M H. Expanding the activity of tissue inhibitors of metalloproteinase (TIMP)-1 against surface-anchored metalloproteinases by the replacement of its C-terminal domain: Implications for anti-cancer effects [J]. PloS one, 2015, 10 (8): e0136384.

Specific procedures are as follows:
1. 1×10$^5$ of unmodified, TIMP-1 or T1$^{PraTACE}$-transduced HT1080 cells were seeded in triplicates in a 24-well plate and cultured overnight.
2. 0.1 μg of HB-EGF/TNF-α plasmid was transfected into the cells and cultured for 2 days.
3. To induce shedding by TACE, the culture medium was replaced with fresh DMEM containing 200 ng/mL phorbol-12-myristate-13-acetate (PMA) (or no PMA as controls). Shedding was allowed for 3 hours at 37° C.
4. Media containing shed HB-EGF/TNF-α was collected and used for analysis.
5. Colorimetric assay on HB-EGF (−PMA/+PMA 200 ng/ml) was conducted by adding the media to an alkaline phosphate substrate in diethanolamine buffer at 37° C. until a change in color was detected.
6. The amount of HB-EGF released was read by a microplate reader
7. The amount of shed TNF-α (−PMA/+PMA 200 ng/ml) was assayed using a TNF-α ELISA kit (Sino Bio).

Result: The lower level of soluble HB-EGF and TNF-α detected in T1$^{PraTACE}$ media indicates that T1$^{PraTACE}$ is more efficient at TACE inhibition than wild type TIMP-1.

Example 5: Unlike Wild Type TIMP-1. T1$^{PraTACE}$ has No Cell Potentiation Activity Materials: T175 flasks (Corning), cell count wafers (Invitrogen), 1 ml syringes Reagents: 0.4% trypan blue solution (Sigma), DMEM Instruments: automatic cell counter (Invitrogen), caliper, balance Method:
1. Unmodified CaKi-1 cells and CaKi-1 cells stably expressing wild type TIMP-1 or T1$^{PraTACE}$ were cultured in 20-cm dishes until the number of cells required was reached.
2. The cells were resuspended in DMEM to the concentration of 2×10$^6$ cells/mL for each cell type.
3. NOD/SCID mice were randomly divided into three groups, namely: control group, TIMP-1 group and T1$^{PraTACE}$ group, each consisting of eight mice.
4. 2×10$^5$ of cells (equivalent to 0.1 mL of cell suspension) were injected subcutaneously into the left and right flanks of the mouse abdomens.
5. Tumor formation was monitored for 35 days with a digital caliper.
6. At the end of the experiment, the mice were sacrificed and the tumors collected and weighed.

Figure 6:
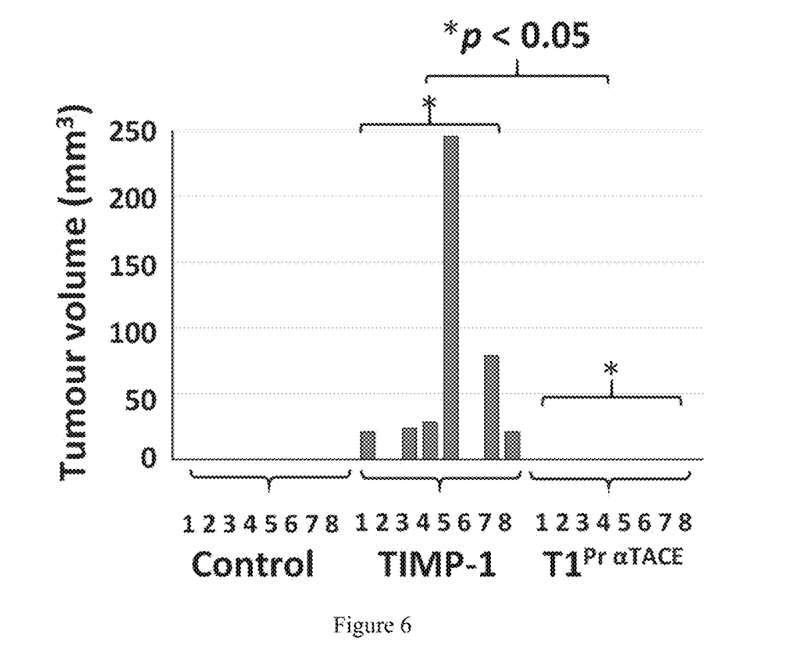
FIG. 6 shows the findings from an in vivo experiment carried out using NOD/SCID mice that proves that T1$^{PraTACE}$ lacks cell potentiation activity on CaKi-1 renal carcinoma cells.
Figure 7:
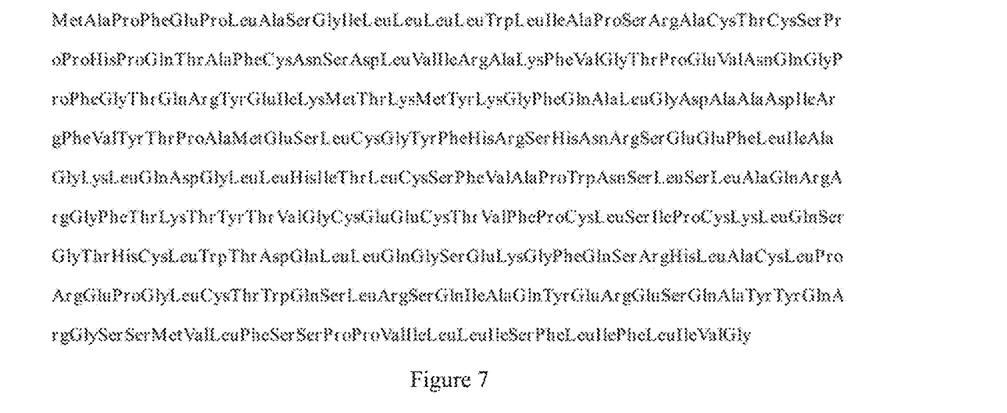
FIG. 7 illustrates the amino acid sequence of T1$^{PraTACE}$ in the present application.

Results: FIG. 6, of the eight mice implanted with TIMP-1-expressing CaKi-1 cells, six developed tumors of various sizes ranging between 20 mm$^3$ and 248 mm$^3$ in volumes. In contrast, no tumor was found in mice from the control and T1$^{PraTACE}$ groups (*p<0.05). The result shows that, unlike the wild type TIMP-1, T1$^{PraTACE}$ has no cell potentiation activity.

Example 6: Preparation and Detection of BHK-21 Cells Expressing T1$^{PraTACE}$ (Named BHK+T1$^{PraTACE}$)

1. BHK-21 cells were transduced with lentivirus bearing T1$^{PraTACE}$ or wild type TIMP-1 genes as described in Example 2.1. Stable cell line selection was carried out with puromycin (named BHK+T1$^{PraTACE}$ hereafter).
2. BHK+T1$^{PraTACE}$ cells were seeded onto a chamber slide, fixed, blocked, rinsed and incubated overnight with TIMP-1 antibody (Abcam, ab1827).
3. The slide was rinsed three times with PBS and incubated with a secondary antibody at room temperature for 2 hours.
4. Following washing with PBS, the cells were inspected with a fluorescence microscope.

Figure 8:
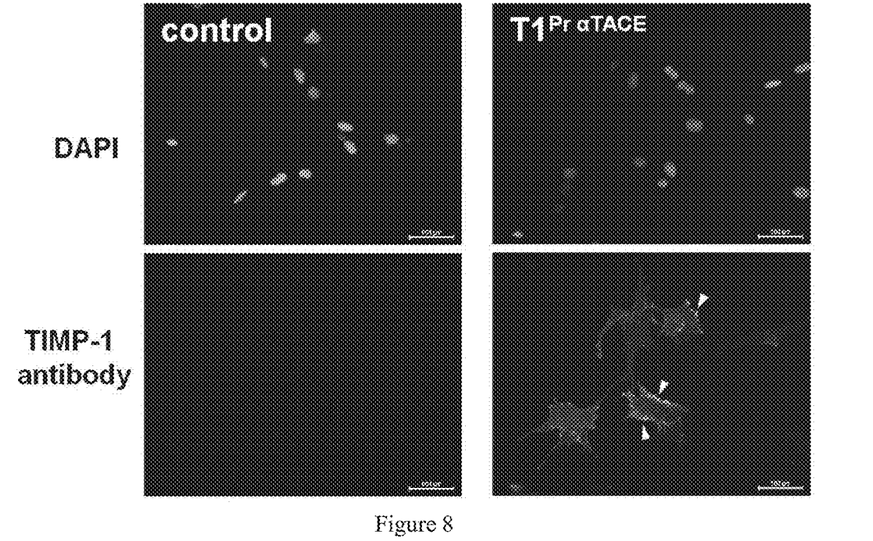
FIG. 8 contains immunostaining images that show the membrane localization of T1$^{PraTACE}$ on BHK+T1$^{PraTACE}$ cell surface.

Result: FIG. 8, Upper panel: nucleus staining with 4',6-diamine-2-phenylindole (DAPI).

Lower panel: whilst no trace of TIMP-1 could be found on the surface of unmodified BHK-21 cells. TIMP-1 was found to be present in abundance on the surface of BHK+T1$^{PraTACE}$ cells.

Example 7: BHK+T1$^{ProTACE}$:Matrigel® Composition Inhibits CaKi-1 Renal Carcinoma Cell Proliferation Method:
1. For the ease of identification, Caki-1 cells were stably transduced with a lentivirus bearing a RFP (purchased from Genomeditech Co., Ltd.).
2. BHK+T1$^{ProTACE}$ and CaKi-1 cells were premixed at the final concentration of $2.5 \times 10^5$ cells/mL for each cell type (1:1 ratio) on ice in 50% Matrigel/DMEM supplemented with 5% FBS.
3. The cell-Matrigel mixture was dispensed as 8 µL micro droplets onto the center of the wells of a 24-well tissue culture plate and allowed to solidify for at least 30 minutes in a 37° C. incubator before 1 mL DMEM/5% FBS was added to the wells.
4. Incubation was allowed for up to 37 days.
5. At the end of the incubation period, the cells were inspected and photographed with a fluorescence microscope.

Figure 9:
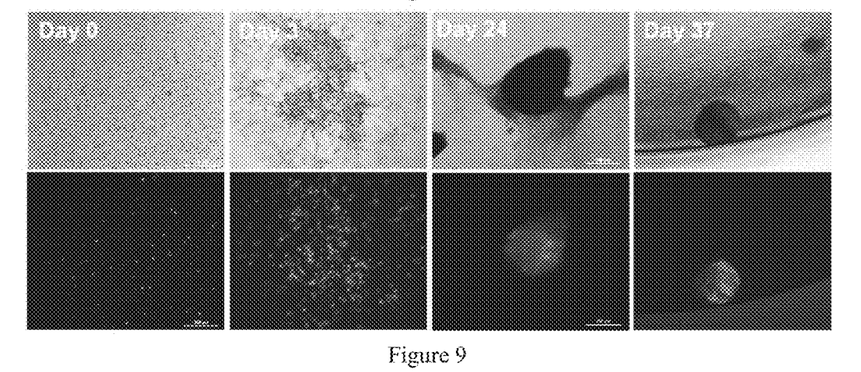
FIG. 9 shows the encapsulation and inhibitory effects the BHK+T1$^{PraTACE}$:Matrgel® composition has on CaKi-1 renal carcinoma cells.

Results: FIG. 9: BHK+T1$^{ProTACE}$ formed spheroid-like structure, capturing within the structure CaKi-1 cells that happened to be in the vicinity.

Control Example 1: Comparing the Inhibitory Potency of BHK-21 and BHK+T1$^{ProTACE}$ Spheroids on Caki-1 Growth Method:
1. BHK+T1$^{ProTACE}$ group: BHK+T1$^{ProTACE}$ and CaKi-1 cells were premixed at the final concentration of $2.5 \times 10^5$ cells/mL for each cell type (1:1 ratio) on ice in 50% Matrigel/DMEM supplemented with 5% fetal bovine serum (FBS). The cell-Matrigel mixture was dispensed as 8 µL micro droplets onto the center of the wells of a 24-well tissue culture plate and allowed to solidify for at least 30 minutes in a 37° C. incubator before 1 mL DMEM/5% FBS was added to the wells.
2. Unmodified BHK-21 group: BHK+T1$^{ProTACE}$ cells were replaced by the same number of unmodified BHK-21 cells following the exact procedure as described in step (1) above.
3. Control group: RFP-labelled CaKi-1 cells were cultured in the absence of BHK-21 cells, following the same procedure/medium as described in step (1) above.

At the end of the incubation period, the number of fluorescent CaKi-1 cells in the spheroids was counted, averaged and analyzed.

Figure 10:
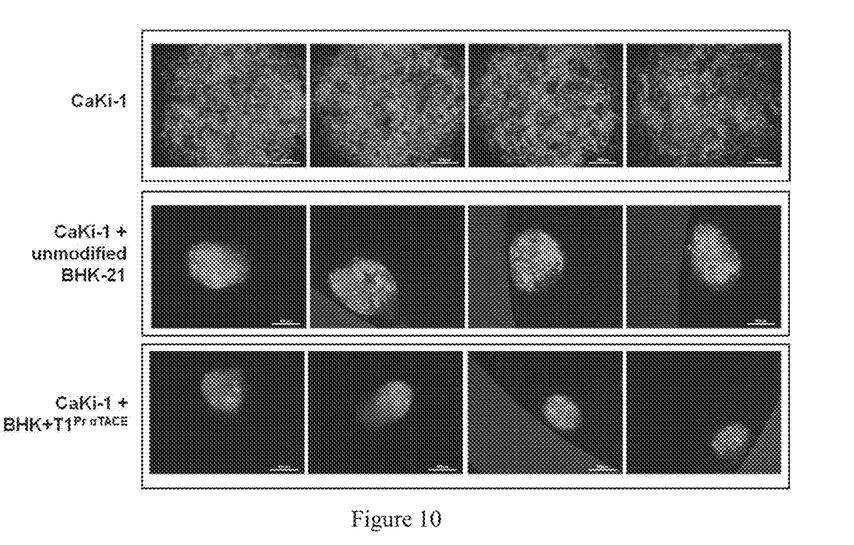
FIG. 10 are images captured with a fluorescent microscope that demonstrate the anti-proliferative effects that (i) BHK+T1$^{PraTACE}$:Matrigel® composition and (ii) BHK:Matrigel® composition have on Caki-1 cells (samples in quadruplet). As shown, BHK+T1$^{PraTACE}$ cells are more effective at encapsulating and inhibiting CaKi-1 cells than unmodified BHK-21 cells.
Figure 11:
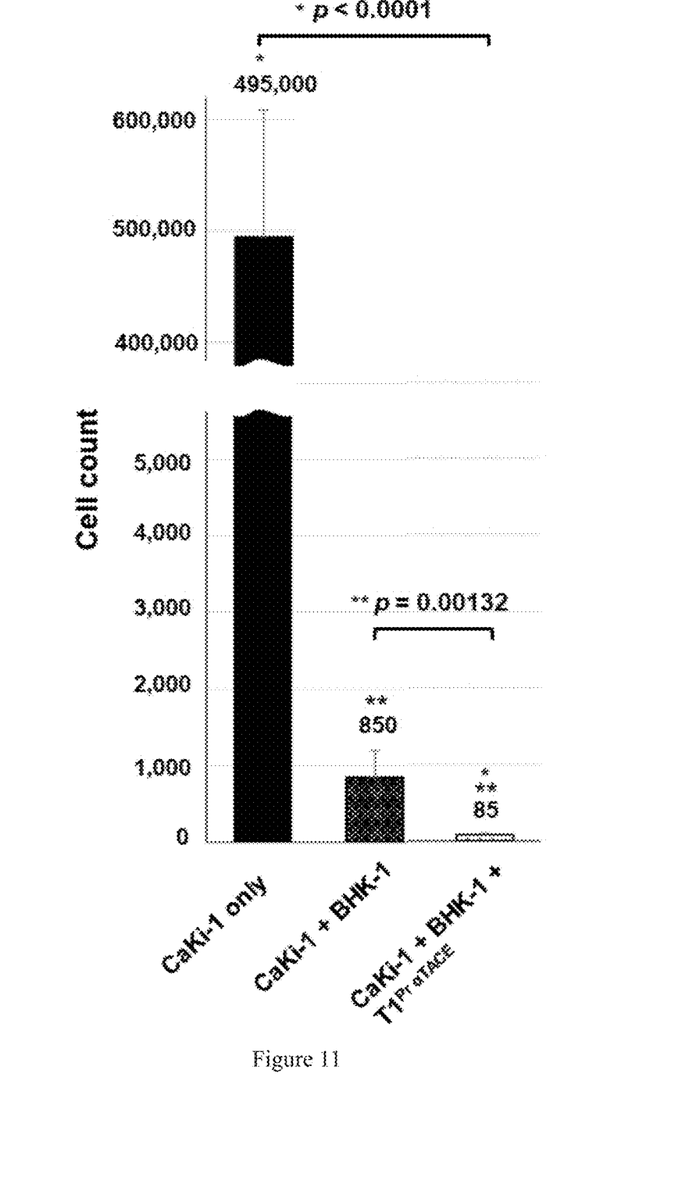
FIG. 11 summarizes the number of surviving Caki-1 cells from the BHK+T1$^{PraTACE}$ group, unmodified BHK-21 group and control group after 37 days of incubation. In all, there are far fewer CaKi-1 cells that survived the BHK+T1$^{PraTACE}$ group than the other groups (p<0.005).

Result I:
FIG. 10: BHK-21 expressing T1$^{ProTACE}$ demonstrated a significantly better anti-proliferative and anti-growth activities on CaKi-1 cells than unmodified BHK-21 cells.

Result II:
At the end of the incubation, the number of RFP-labelled cancer cells in the spheroid was counted, averaged and analyzed.

As shown in Table 2: the number of surviving CaKi-1 cells in the BHK+T1$^{ProTACE}$ group was only one tenth of that of the unmodified BHK-21 group (p=0.00132). The data further strengthen the finding that BHK+T1$^{ProTACE}$ cells are more effective at CaKi-1 inhibition than unmodified BHK-21 cells.

TABLE 2

| | Number of seeded CaKi-1 cells | Number of surviving CaKi-1 cells after 37 days |
|---|---|---|
| CaKi-1 | 5,000 | 495,000 ± 113,812 |
| CaKi-1 + BHK-21 | 5,000 | 850 ± 339 |
| CaKi-1 + BHK-21 + T1$^{ProTACE}$ | 5,000 | 85 ± 13 |

Control Example 2: Comparing the Inhibitory Potency of BHK-21 and BHK+T1$^{ProTACE}$ Spheroids on HeLa Cell Growth Method: the procedure employed for HeLa cells in this case was identical to those of the Control example 1 (CaKi-1).

Figure 12:
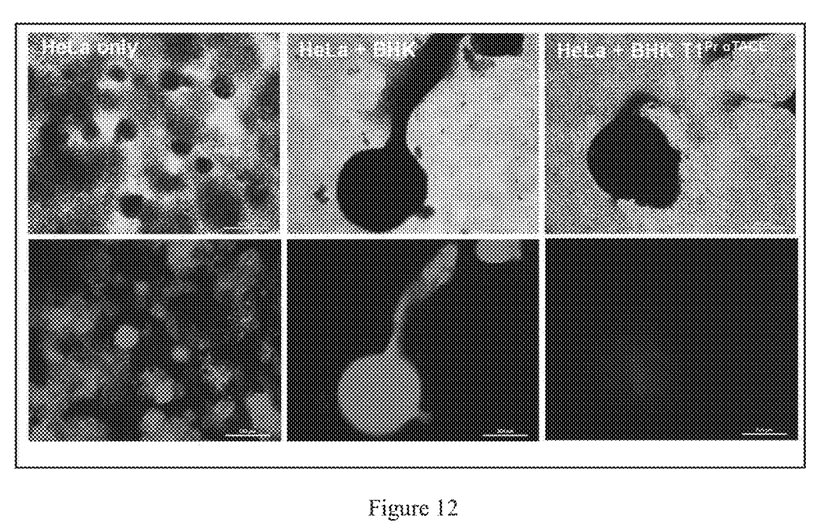
FIG. 12 contains microscope images that illustrate the relative fluorescent intensity of surviving HeLa cells in the BHK+T1$^{PraTACE}$ group, unmodified BHK-21 group and control group towards the end of incubation. As with CaKi-1 cells in FIG. 10, BHK+T1$^{PraTACE}$ cells are far more superior than unmodified BHK-21 cells in hindering HeLa cell proliferation.

Result I:
FIG. 12: the fluorescence intensity of surviving HeLa cells in the BHK+T1$^{ProTACE}$ group was much lower than that of the unmodified BHK-21 group. The data show that BHK+T1$^{ProTACE}$ cells are more effective in encapsulating and restricting the growth of HeLa cells than unmodified BHK-21 cells.

Figure 13:
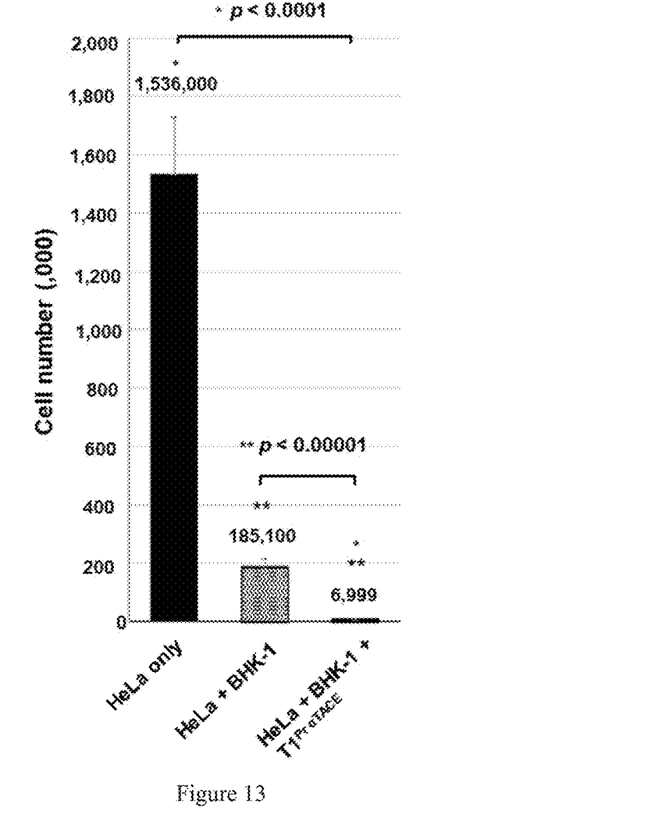
FIG. 13 is a summary of the number of surviving HeLa cells from the BHK+T1$^{PraTACE}$ group, unmodified BHK-21 group and control group at the end of incubation. Again, there are far fewer HeLa cells that survived the BHK+T1$^{PraTACE}$ group than the other groups (p<0.00001).

Result II:
FIG. 13: the number of surviving HeLa cells was counted, averaged and analyzed at the end of the 28-day incubation period.

Table 3 show that the number of surviving HeLa cells in BHK+T1$^{ProTACE}$ group was significantly lower than that of the unmodified BHK-21 group (p<0.0001).

TABLE 3

| | Number of seeded HeLa cells | Number of surviving HeLa cells after 28 days |
|---|---|---|
| HeLa-1 | 5,000 | 1,536,000 ± 195,414 |
| HeLa + BHK-21 | 5,000 | 185,100 ± 29,639 |
| HeLa + BHK-21 + T1$^{ProTACE}$ | 5,000 | 6,999 ± 4,858 |

Results from the study confirm that BHK+T1$^{ProTACE}$ is more effective in inhibiting HeLa cells than unmodified BHK-21 cells.

Data presented above illustrate and describe the basic principles, main features and advantages of the present invention. It must be understood by those skilled in the art that the present invention is not limited to the above embodiments. The above embodiments and description merely describe the principles of the present invention. Various modifications and improvements may be made to the present invention without departing from the spirit and scope of the present invention. These modifications and improvements are within the scope of the present invention. The scope of the present invention is defined by the appended claims and equivalents thereof.

The invention claimed is:

1. A membrane-type metalloprotease inhibitory protein T1$^{PraTACE}$ comprising the amino acid sequence of Seq ID No. 1.

2. A drug, comprising the membrane-type metalloprotease inhibitory protein T1$^{PraTACE}$ of claim 1 and a pharmaceutically acceptable excipient.

3. The drug of claim 2, wherein the excipient is a carrier, a solvent, a emulsifier, a dispersant, a humectant, an adhesive, a stabilizer, a colorant or a flavor.

4. The drug of claim 2, wherein the drug is a tablet.

* * * * *

SEQUENCE LISTING

<160> NUMBER OF SEQ ID NOS: 10

<210> SEQ ID NO 1
<211> LENGTH: 245
<212> TYPE: PRT
<213> ORGANISM: Artificial sequence
<220> FEATURE:
<223> OTHER INFORMATION: amino sequence of modified T1PralphaTACE

<400> SEQUENCE: 1

```
Met Ala Pro Phe Glu Pro Leu Ala Ser Gly Ile Leu Leu Leu Leu Trp
1               5                   10                  15

Leu Ile Ala Pro Ser Arg Ala Cys Thr Cys Ser Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Gly Pro Phe Gly Thr Gln Arg Tyr Glu Ile
    50                  55                  60

Lys Met Thr Lys Met Tyr Lys Gly Phe Gln Ala Leu Gly Asp Ala Ala
65                  70                  75                  80

Asp Ile Arg Phe Val Tyr Thr Pro Ala Met Glu Ser Leu Cys Gly Tyr
                85                  90                  95

Phe His Arg Ser His Asn Arg Ser Glu Glu Phe Leu Ile Ala Gly Lys
            100                 105                 110

Leu Gln Asp Gly Leu Leu His Ile Thr Leu Cys Ser Phe Val Ala Pro
        115                 120                 125

Trp Asn Ser Leu Ser Leu Ala Gln Arg Arg Gly Phe Thr Lys Thr Tyr
    130                 135                 140

Thr Val Gly Cys Glu Glu Cys Thr Val Phe Pro Cys Leu Ser Ile Pro
145                 150                 155                 160

Cys Lys Leu Gln Ser Gly Thr His Cys Leu Trp Thr Asp Gln Leu Leu
                165                 170                 175

Gln Gly Ser Glu Lys Gly Phe Gln Ser Arg His Leu Ala Cys Leu Pro
            180                 185                 190

Arg Glu Pro Gly Leu Cys Thr Trp Gln Ser Leu Arg Ser Gln Ile Ala
        195                 200                 205

Gln Tyr Glu Arg Glu Ser Gln Ala Tyr Tyr Gln Arg Gly Ser Ser Met
    210                 215                 220

Val Leu Phe Ser Ser Pro Pro Val Ile Leu Leu Ile Ser Phe Leu Ile
225                 230                 235                 240

Phe Leu Ile Val Gly
                245
```

<210> SEQ ID NO 2
<211> LENGTH: 738
<212> TYPE: DNA
<213> ORGANISM: Artificial sequence
<220> FEATURE:
<223> OTHER INFORMATION: DNA sequence of modified T1PralphaTACE

<400> SEQUENCE: 2

```
atggcccct  ttgagcccct  ggcttctggc  atcctgttgt  tgctgtggct  gatagccccc      60
agcagggcct  gcacctgttc  cccacccca   ccacagacgg  ccttctgcaa  ttccgacctc    120
gtcatcaggg  ccaagttcgt  ggggacacca  gaagtcaatc  agggtccgtt  cggcacccag    180
cgttatgaga  tcaagatgac  caagatgtat  aaagggttcc  aagccttagg  ggatgccgct    240
gacatccggt  tcgtctatac  ccccgccatg  gagagtctct  gcggatactt  ccacaggtcc    300
```

```
cacaaccgca gcgaggagtt tctcattgct ggaaaactgc aggatggact cttgcacatc    360
actctctgca gtttcgtggc tccctggaac agcctgagct tagctcagcg ccggggcttc    420
accaagacct acactgttgg ctgtgaggaa tgcacagtgt ttccctgttt atccatcccc    480
tgcaaactgc agagtggcac tcattgcttg tggacggacc agctcctcca aggctctgaa    540
aagggcttcc agtcccgtca ccttgcctgc ctgcctcggg agccagggct gtgcacctgg    600
cagtccctgc ggtcccagat agcccagtac gagagggaat ctcaggccta ttaccagaga    660
ggatcgagca tggtcctctt ctcctcccca cctgtgatcc tcctgatctc tttcctcatc    720
ttcctaatag tgggatga                                                  738

<210> SEQ ID NO 3
<211> LENGTH: 34
<212> TYPE: DNA
<213> ORGANISM: Artificial sequence
<220> FEATURE:
<223> OTHER INFORMATION: primer

<400> SEQUENCE: 3
gaaccatatg tgcacctgtg taccaccccca ccca                                34

<210> SEQ ID NO 4
<211> LENGTH: 64
<212> TYPE: DNA
<213> ORGANISM: Artificial sequence
<220> FEATURE:
<223> OTHER INFORMATION: primer

<400> SEQUENCE: 4
tcaactgctc gagttaatga tgatgatgat gatgatgatg ggctatctgg gaccgcaggg    60
actg                                                                  64

<210> SEQ ID NO 5
<211> LENGTH: 34
<212> TYPE: DNA
<213> ORGANISM: Artificial sequence
<220> FEATURE:
<223> OTHER INFORMATION: primer

<400> SEQUENCE: 5
gaaccatatg tgcacctgtt ccccaccccca ccca                                34

<210> SEQ ID NO 6
<211> LENGTH: 39
<212> TYPE: DNA
<213> ORGANISM: Artificial sequence
<220> FEATURE:
<223> OTHER INFORMATION: primer

<400> SEQUENCE: 6
gcagcagaat tcaccatggc cccctttgag ccctggct                             39

<210> SEQ ID NO 7
<211> LENGTH: 40
<212> TYPE: DNA
<213> ORGANISM: Artificial sequence
<220> FEATURE:
<223> OTHER INFORMATION: primer

<400> SEQUENCE: 7
tcaactgggg cccttaggct atctgggacc gcagggactg                           40
```

```
<210> SEQ ID NO 8
<211> LENGTH: 48
<212> TYPE: DNA
<213> ORGANISM: Artificial sequence
<220> FEATURE:
<223> OTHER INFORMATION: primer

<400> SEQUENCE: 8
ggcctgagat tccctctcgt actgggctat ctgggaccgc agggactg            48

<210> SEQ ID NO 9
<211> LENGTH: 72
<212> TYPE: DNA
<213> ORGANISM: Artificial sequence
<220> FEATURE:
<223> OTHER INFORMATION: primer

<400> SEQUENCE: 9
cacaggtggg gaggagaaga ggaccatgct cgatcctctc tggtaatagg cctgagattc    60
cctctcgtac tg                                                        72

<210> SEQ ID NO 10
<211> LENGTH: 77
<212> TYPE: DNA
<213> ORGANISM: Artificial sequence
<220> FEATURE:
<223> OTHER INFORMATION: primer

<400> SEQUENCE: 10
taaacgggcc ctcatcccac tattaggaag atgaggaaag agatcaggag gatcacaggt    60
ggggaggaga agaggac                                                   77
```